US008644956B2

United States Patent
Kolberg et al.

(10) Patent No.: US 8,644,956 B2
(45) Date of Patent: Feb. 4, 2014

(54) SHOCK ELECTRODE LINE

(75) Inventors: Gernot Kolberg, Berlin (DE); Klaus Bartels, Berlin (DE); Thomas Guenther, Michendorf (DE)

(73) Assignee: Biotronik CRM Patent AG, Baar (CH)

( * ) Notice: Subject to any disclaimer, the term of this patent is extended or adjusted under 35 U.S.C. 154(b) by 723 days.

(21) Appl. No.: 12/482,324

(22) Filed: Jun. 10, 2009

(65) Prior Publication Data
US 2010/0010605 A1    Jan. 14, 2010

(30) Foreign Application Priority Data
Jul. 8, 2008    (DE) .......................... 10 2008 040 254

(51) Int. Cl.
*A61N 1/05*    (2006.01)

(52) U.S. Cl.
USPC ............... 607/122; 607/116; 607/119; 607/4; 607/5

(58) Field of Classification Search
USPC .......................... 607/115–119, 122, 125, 4, 5
See application file for complete search history.

(56) References Cited

U.S. PATENT DOCUMENTS

| | | |
|---|---|---|
| 5,203,348 A | 4/1993 | Dahl et al. |
| 5,314,459 A | 5/1994 | Swanson et al. |
| 5,531,766 A | 7/1996 | Kroll et al. |
| 5,534,022 A | 7/1996 | Hoffmann et al. |
| 5,658,709 A | 8/1997 | Layman et al. |
| 5,662,697 A * | 9/1997 | Li et al. ............. 607/122 |
| 5,728,149 A * | 3/1998 | Laske et al. ......... 607/122 |
| 6,030,382 A * | 2/2000 | Fleischman et al. ..... 606/41 |
| 6,449,506 B1 | 9/2002 | Sh. Revishvili et al. |
| 6,684,109 B1 | 1/2004 | Osypka |
| 2005/0228470 A1 | 10/2005 | Osypka |

FOREIGN PATENT DOCUMENTS

WO    WO 02/22202    3/2002

OTHER PUBLICATIONS

European Search Report, dated Sep. 7, 2009.
German Search Report, dated May 8, 2009.

* cited by examiner

*Primary Examiner* — Joseph Stoklosa
(74) *Attorney, Agent, or Firm* — Arc IP Law, PC; Joseph J. Mayo

(57) ABSTRACT

Implantable shock electrode line having a proximal end for connection to an implantable device which generates shock pulses, and a distal segment which has a shock electrode, wherein an area ratio of the shock electrode area to the surface area of the shock electrode line is not constant over the longitudinal extent of the shock electrode.

7 Claims, 4 Drawing Sheets

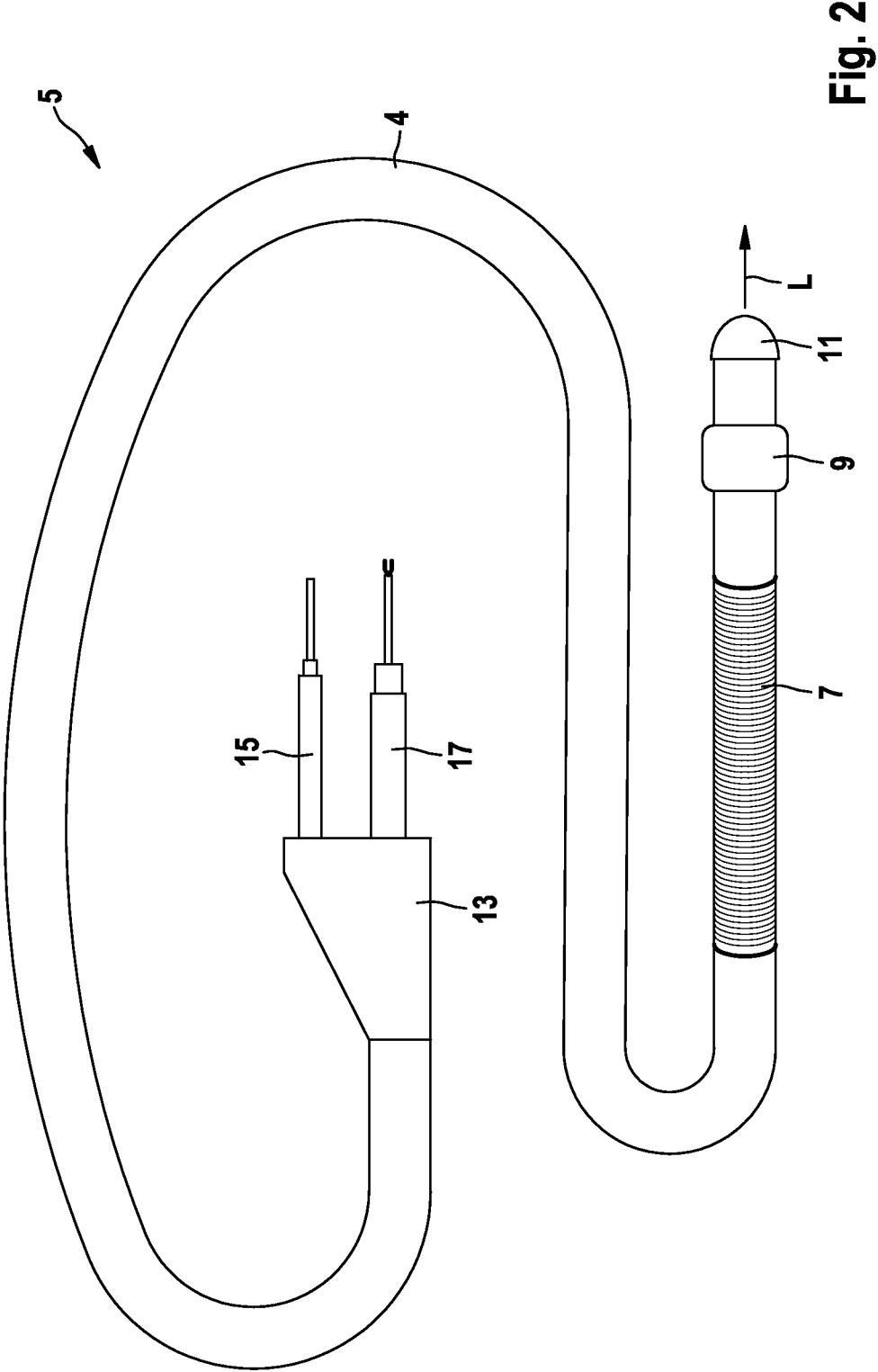

SHOCK ELECTRODE LINE

This application takes priority from German Patent Application DE 10 2008 040 254.0, filed 8 Jul. 2008, the specification of which is hereby incorporated herein by reference.

BACKGROUND OF THE INVENTION

1. Field of the Invention

The invention relates to an implantable shock electrode line for treating a biological tissue and/or an organ with electroshock therapy and an implantable shock electrode arrangement.

2. Description of the Related Art

Implantable electrode lines, in particular cardiac electrode lines for endocardial sensing of cardiac action potentials and/or for electric stimulation or defibrillation of the heart are already known in a wide variety and have long been in practical use on a large scale in combination with implanted cardiac pacemakers or defibrillators. Endocardial systems (ICDs) dramatically reduce morbidity and mortality and make the therapeutic process a realistic option for large groups of patients.

FIG. 1 shows the basic design of an implantable defibrillation arrangement 1, such as that known from U.S. Pat. No. 5,531,766. To stimulate the heart H of a patient P, a defibrillator 3 is electrically connected to an electrode line 5 having at least one electrode ("shock electrode") 7, which is located at its distal end and is placed in the patient's heart. As a rule, defibrillation is performed via a current path between this electrode and a counter electrode located a greater or lesser distance away from the heart to be stimulated. The position and structure of the electrode play an important role in efficient stimulation and/or defibrillation. The housing 8 of the defibrillator 3 containing the units for detection of heart signals and for generating electric pulses may act as counter electrodes. Alternatively, a counter electrode may also be mounted on the outside of the housing.

Like a pacemaker implantation, the ICD method involves access via the cephalic vein or the subclavian vein and positioning of a defibrillation probe in the right ventricle. ICD probes having a single shock electrode for placement in the right ventricle are available or have a second electrode positioned further proximally, typically in the right atrium, in the superior vena cava or in the subclavian vein.

In addition, "hot can" systems offer two possible configurations: a "single-coil" probe with the shock vector from the right ventricle to the ICD housing (referred to as unipolar) and a "dual coil" probe with a defibrillation field between the right ventricle, the superior vena cava and the housing ("triad" configuration).

U.S. Pat. No. 5,203,348 describes a defibrillation electrode for subcutaneous administration in the form of a spiral design with a large area, forming the distal end of the feeder line of the defibrillation electrode. The coiled shape is used here to increase the effective electrode surface area.

The coil-like shock electrodes are coiled from one or more parallel wires, strips or small coils. The electric resistance here is constant over the length of the wire and/or strip.

The current density distribution of a coil-like electrode depends on the electrically active surface area, the electric resistance of the coil material and, apart from the body structures of the patient, the location of the electrodes relative to one another, so the current density distribution can be influenced only to a limited extent with traditional designs. Furthermore, an electric shock administered to the heart or chest does not produce a perfectly uniform electric field. In a so-called "dual-coil system," the shock coils are arranged in succession, for example, rather than being axially parallel, so that the tissue and/or organs between the electrodes is/are exposed to a heterogeneous field distribution. In regions of a higher field strength (typically close to the defibrillation electrode), the myocardium has greater effects in depolarization and repolarization than cells in the weaker electric field. This known variability of the cellular response in a heterogeneous shock field is known as a "graded response."

The defibrillation threshold (DFT) is an important factor that must be taken into account in defibrillation therapy. The defibrillation threshold corresponds to the lowest shock energy with which ventricular fibrillation is in fact terminated. The defibrillation threshold depends on the cardiac cells reached "last," so it is possible to assume that when there is an uneven field distribution, certain tissue zones are supplied with too much energy in an unnecessary manner. With a balanced field distribution, however, the DFT can be lowered.

The electric field can be influenced by changing the polarity of the shock electrodes as disclosed in U.S. Pat. No. 6,449,506. However, this makes it possible to adjust the transition impedance to the electrolyte only within narrow limits. The transition impedance to the electrolyte is understood to refer to the total resistance of the current path between the shock electrode and the counter electrode through an electrolytic material (tissue, organ, blood).

BRIEF SUMMARY OF THE INVENTION

The object of the invention is therefore to provide an improved implantable shock electrode line and/or a corresponding shock electrode arrangement which allows the use of a reduced shock energy with the same efficacy.

This object is achieved according to a first aspect of the invention by an implantable shock electrode line having the features as claimed herein and according to a second aspect of the invention by an implantable shock electrode arrangement having the features that further include and an implantable device having a housing which acts as a counter electrode. Expedient refinements of the inventive idea are the subject of the dependent claims.

The inventive shock electrode line is characterized in that an area ratio of the shock electrode area to the surface area of the shock electrode line over the longitudinal extent of the shock electrode is not constant. This offers a great tolerance in the design of shock electrode lines. The mechanical properties as well as the electric resistance of the shock electrode and the transition impedance to the electrolyte can therefore be adjusted in a targeted manner through the length of the shock electrode. Thus, on the one hand, the current density distribution in the case of the ICD shock and, on the other hand, the mechanical properties of the shock electrode can be influenced in a targeted manner. The design possibilities can be utilized to lower the defibrillation threshold, to influence the initial growth behavior, to prevent the risk of perforation and to increase the durability of the shock electrode. Furthermore, the rigidity of the shock electrode over its length can be influenced in a targeted manner in this way, thereby minimizing the mechanical irritation, e.g., in the heart.

In a design in which the distal end of the shock electrode is the farthest removed from the counter electrode, the transition impedance to the electrolyte and/or the total resistance over the resulting current path is the greatest. It follows from this that the tissue zones are exposed to a relatively low energy shock at this location. A preferred embodiment of the invention consists of the fact that the area ratio of the shock electrode area increases toward the distal end of the shock electrode. In this way, the amperage at the distal end of the electrode and thus also the shock energy input are increased at the tissue zones adjacent there. A balanced field distribution is achieved through this measure, leading to a reduction in the defibrillation threshold in a defibrillation process.

Alternatively, the area ratio of the shock electrode area may decrease toward the distal end of the shock electrode or may otherwise vary over the length of the electrode, depending on how the overall configuration of the cardioversion arrangement should look and in which concrete manner the electric field is to be varied at different locations in the shock electrode.

To further influence the electric field generated by the shock electrode, the current may be directed at least partially directly to the distal end of the electrode. The series resistance of the shock electrode segment on the distal end is thus lower than the series resistance of the remaining segment. Since the transition impedance to the electrolyte depends directly on the internal electrode resistance, the direct current feed at the distal end of the electrode leads to a reduction in the transition impedance of the electrolyte there.

A technologically expedient embodiment provides for a shock electrode which is designed as a tube. The tube which ensures a more stable structure of the electrode has a core of an insulating material (silicone or a similar polymer). On the surface of this tube is arranged a conductive structure, which corresponds to the active electric shock electrode area and is in direct contact with the tissue and/or organ to be stimulated.

The conductive structure is preferably designed as a multilayer structure. It has at least two layers of differing conductivity. The first layer arranged on the surface of the tube may consist of tantalum, which has a good electric conductivity and mechanical stability, while the second layer, i.e., the cover material, consists of biocompatible platinum or a platinum-iridium alloy.

Alternatively, the conductive structure may be arranged on a layer of shape memory alloy (memory metal), which coats the entire tube. Such alloys, e.g., nickel-titanium alloys (nitinol) may also apparently "remember" a previous shape despite subsequent extreme deformation. This is especially beneficial if the shape of the electrode is to be altered after implantation.

The multilayer structure may already be formed in drawing of the tube. Several tubes made of different materials are placed one inside the other and drawn to the desired diameter. Alternatively, the layers may be formed on a core tube by an electroplating process and/or by vapor-phase deposition or by sputtering.

The conductive structure may assume different shapes due to a laser cutting or etching process. With these cut structures, the mechanical properties (bending and torsional stiffness, tensile and compressive stress), the electric properties (resistance) and the coupling to the electrolyte (contact area) may be varied over the length of the shock electrode.

If the core tube is completely coated with a conductive material, the spaces between the cut conductive structures are preferably filled with an insulating material such as silicone rubber, so that only the cover material of the multilayer structure is in electric contact with the tissue and/or organ.

In another embodiment of the invention, the conductive structure has parallel rings of different widths. The width of the rings may vary at different locations in the shock electrode. It may increase and/or decrease toward the distal end of the electrode, for example. To electrically connect the parallel rings, conductive webs are present between the rings.

In an alternative embodiment, the conductive structure has strips of a width that is non-constant, extending over the length of the electrode. These strips may become narrower or wider, for example, toward the distal end of the electrode.

Another alternative embodiment provides a conductive structure, having a coil whose pitch is not constant. The pitch may increase or decrease toward the distal end of the electrode, for example. Similarly, the conductive structure may have a mesh and/or grid structure with at least two interwoven coil structures of a non-constant pitch.

In addition to the coil structure, axial structural elements are also conceivable, e.g., transverse connections between the coils or between other types of surfaces (disks, washers, rings). In one embodiment of the invention, these structural elements may be varied in size over the length of the shock electrode, with the pitch of the coils remaining constant or also being varied.

Another embodiment proposes a conductive structure having layers with a non-constant height along the electrode. The layer height may be different at different locations along the shock electrode, so that different hardness values are provided along the electrode to thereby maintain one or more preferential directions of bending, for example.

The embodiments of the conductive structure on a shock electrode as described above may of course also be combined with one another.

In a somewhat modified embodiment of the invention, the shock electrode is designed as a wire coil (shock electrode coil), the pitch of which is not constant. The coil may be coiled tightly and/or widely toward the distal end of the shock electrode. The pitch may of course vary over the length of the electrode, depending on whether the electric field is to be varied at different locations on the shock electrode.

An inventive implantable shock electrode arrangement is characterized in that one of the shock electrode lines described above is connected at the proximal end to an implantable device, e.g., a defibrillator. This device acts as a counter electrode and has a housing which usually contains a control unit for sensing and/or generating electric pulses and a battery for the power supply.

In particular, in addition to having a sensor, the shock electrode line has a sensor electrode for sensing tissue action potentials and/or an organ action potentials and a stimulation electrode for low-energy electric stimulation.

Sensing electrodes and stimulation electrodes are integrated into a transveous probe, which has a layer-like structure like the layers of an onion (coaxial configuration). Spiral-shaped conductors for detection/stimulation and optionally for defibrillation are provided concentrically from the inside to the outside. There is a separate insulation layer between each of the individual conductors. Advantageously, a multi-lumen design may also be used. The conductors for detection, stimulation and optionally defibrillation are arranged here in parallel within an electrode body, each being sheathed by its own insulation layer. In addition, cavities arranged longitudinally are also provided in the electrode body for stabilization. The advantages of multi-lumen electrodes include a smaller diameter and better long-term stability.

With regard to the long-established implantable shock electrode arrangements, it is advantageous that the inventive arrangement allows a balanced field distribution over the tissue and/or organ zones to be stimulated. In an ICD system, this may lead to a reduction in the defibrillation threshold. It follows from this that the tissue and/or organs are not exposed to an unnecessarily high and possibly harmful energy level and the battery present in the implantable device has a longer lifetime.

BRIEF DESCRIPTION OF THE DRAWINGS

Advantages and expediencies of the invention are otherwise derived from the exemplary embodiments selected from the following description on the basis of the figures, in which:

FIG. 2 shows a schematic diagram of an implantable shock electrode line according to the invention.

DETAILED DESCRIPTION OF THE INVENTION

Figure 1:
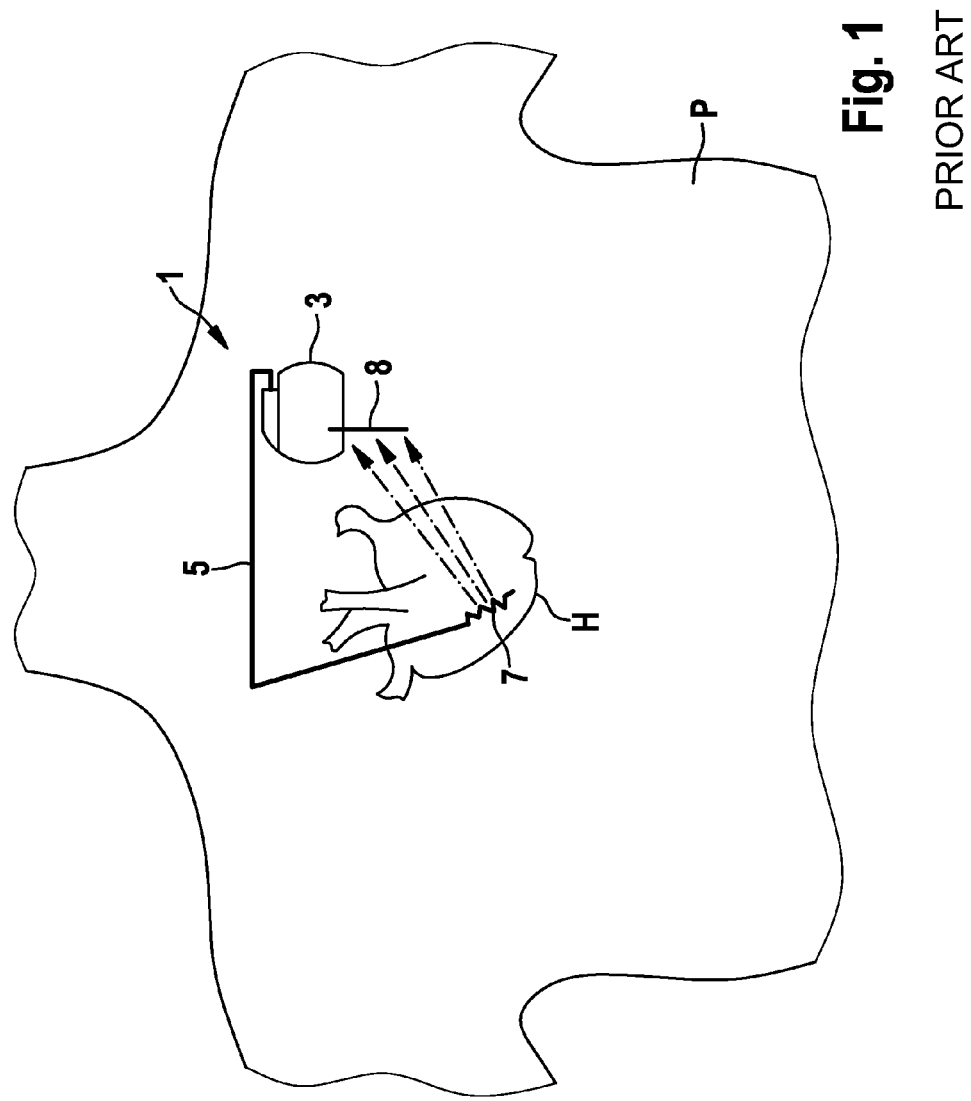
FIG. 1 shows a schematic diagram of an ICD arrangement.

FIG. 2 shows an implantable shock electrode line 5, which has a flexible plastic tubing 4 with a proximal end and a distal segment.

In the distal segment, the shock electrode line 5 has an elongated shock electrode 7, which is placed in contact with the wall in a patient's heart and a ring electrode 9 and a tip electrode 11, which are provided for sensing and/or stimulation purposes. On the proximal end, plug elements 15, 17 are provided, extending from a Y-distributor 13 and assigned to the shock electrode 7 and to the stimulation and/or detection electrodes 9, 11 and connected electrically to an implantable device (not shown).

Figure 3A:
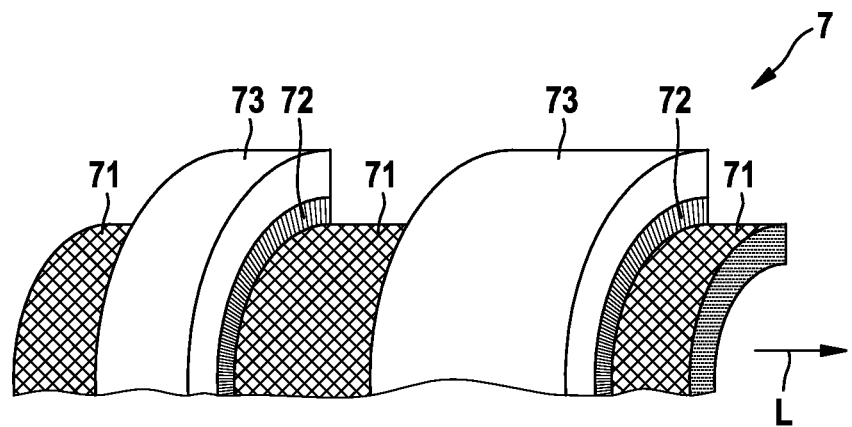
FIGS. 3A and 3B show schematic diagrams of a segment of the shock electrode according to one embodiment of the invention.

FIG. 3A shows a segment of the shock electrode 7 designed as a tube. A two-layer semiconductive structure is arranged on the core tube 71. The first layer 72, which is in direct contact with the core tube 71, consists of a material have a higher conductivity in comparison with the material of a second layer 73, which covers the first layer 72 but has better biocompatibility than that one.

Figure 3B:
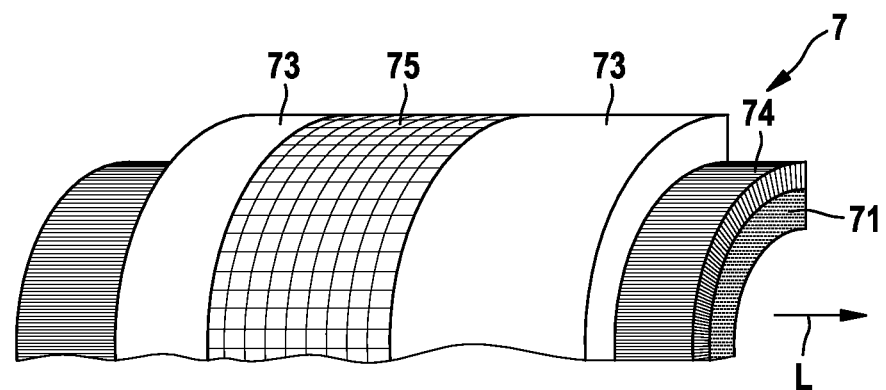

FIG. 3B shows a variant of the embodiment of FIG. 3A. The conductive structure, which is formed here only by the cover layer 73, is arranged on a layer of shape memory alloy 74 coating the core tube 71. The distances here between the conductive structures are filled with an insulating material 75, so that the cover layer 73 corresponds to the electrically active shock electrode surface, which is in contact with the tissue and/or organ.

Both FIGS. 3A and 3B show clearly here that the width of the active shock electrode area changes over the length L of the electrode.

FIG. 4A to FIG. 4D show possible embodiments of the shock electrode 3, which is designed as a tube.

Figure 4A:
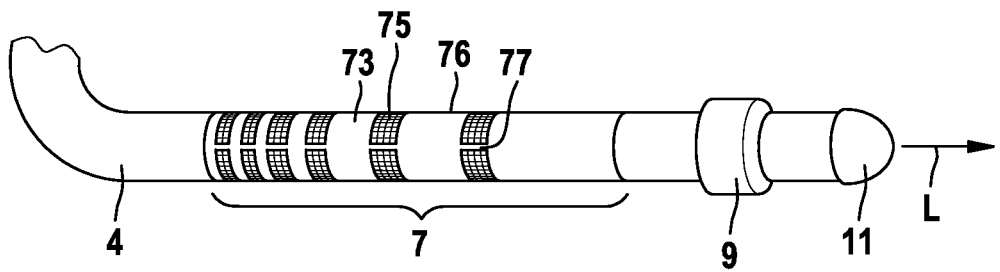
FIGS. 4A to 4D show schematic diagrams of the distal segment of the shock electrode line according to alternative embodiments of the invention.

FIG. 4A shows the distal segment of the shock electrode line 5, where the conductive structure has parallel rings 76 of differing width connected by conductive webs 77. The width of the rings increases toward the distal end of the electrode.

Figure 4B:
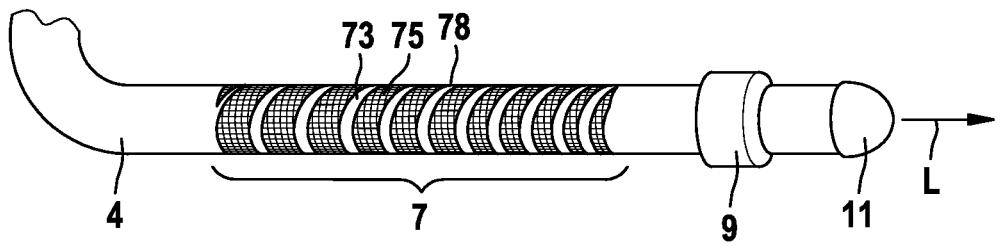

FIG. 4B shows the distal segment of a shock electrode line 5', where the conductive structure has a coil 78. The pitch of the coil increases toward the distal end of the electrode.

Figure 4C:
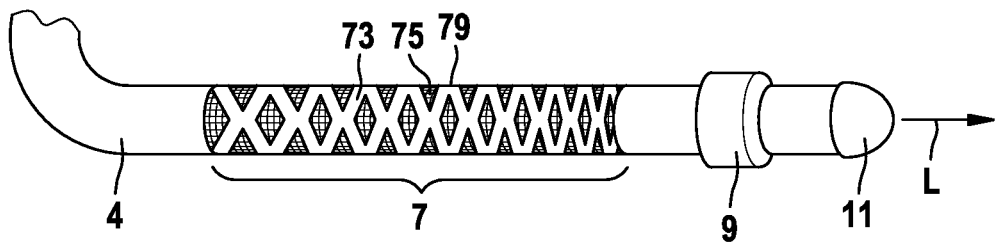

Similarly, FIG. 4C shows the distal segment of a shock electrode line 5" according to another embodiment of the invention, where the conductive structure has a network structure 79, which becomes denser toward the distal end of the electrode.

Figure 4D:
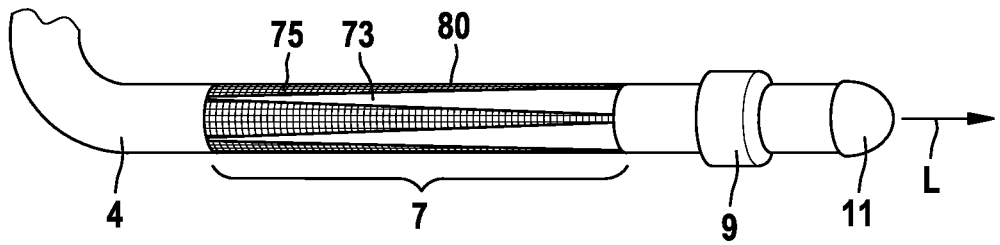

Finally, FIG. 4D shows as another embodiment a shock electrode line 53' in which strips 18 running distally with a width that increases toward the distal end are provided as the conductive surface structure.

This embodiment of the invention is not limited to the examples and features described above but is also possible in a variety of modifications which are within the scope of technical expertise.

What is claimed is:

1. A shock electrode line (5) comprising:
   a proximal end configured to connect to an implantable device (3) wherein said implantable device is configured to generate shock pulses;
   a distal segment having a shock electrode (7);
   wherein an area ratio of the shock electrode to a surface area of the shock electrode line (5) is not constant over a longitudinal extent of the shock electrode (7);
   wherein the shock electrode (7) is configured as a tube with a conductive structure arranged on a surface of the shock electrode (7);
   wherein the conductive structure has a non-constant layer height in a direction away from said tube along the shock electrode (7) so that the layer height is different at different locations along the shock electrode (7) to provide higher and lower hardness values along the shock electrode (7) respectively wherein said shock electrode is configured with at least one preferential bend direction having said lower hardness value;
   wherein the conductive structure has a coil (78), whose pitch is not constant; and,
   wherein the conductive structure has at least two layers (72, 73) with a different conductivity wherein said at least two layers comprise a first layer arranged on a surface of the tube and a second layer arranged on top of said first layer.

2. The shock electrode line (5) according to claim 1, wherein the area ratio of the shock electrode to the surface area of the shock electrode line increases toward the distal segment of the shock electrode (7).

3. The shock electrode line (5) according to claim 1, wherein the conductive structure is formed by a laser cutting process.

4. A shock electrode arrangement (1) comprising a shock electrode line (5) according to claim 1 and wherein the implantable device (3) comprises a housing configured to act as a counter electrode.

5. The shock electrode arrangement (1) according to claim 4, wherein the shock electrode line (1) comprises a sensor (9) configured to sense tissue action potentials and/or organ action potentials and further comprises a stimulation electrode (11) for low-energy energetic stimulation.

6. A shock electrode line (5) according to claim 1 wherein said first layer is tantalum arranged on the surface of the tube and said second layer is biocompatible platinum or a platinum-iridium alloy arranged on top of said first layer.

7. A shock electrode line (5) according to claim 1, wherein the conductive structure is arranged on a layer of shape memory alloy (74).

* * * * *